United States Patent [19]
Bryant et al.

[11] Patent Number: 5,511,540
[45] Date of Patent: Apr. 30, 1996

[54] INHALATION DEVICE

[75] Inventors: Andrew M. Bryant, Loughborough; Anthony C. L. Wass, Stamford, both of Great Britain; Guenter M. Zilligan, Grevenbroich, Germany

[73] Assignee: Minnesota Mining and Manufacturing Company, St. Paul, Minn.

[21] Appl. No.: 381,867

[22] PCT Filed: Aug. 18, 1993

[86] PCT No.: PCT/GB93/01754

§ 371 Date: Feb. 15, 1995

§ 102(e) Date: Feb. 15, 1995

[87] PCT Pub. No.: WO94/04209

PCT Pub. Date: Mar. 3, 1994

[51] Int. Cl.$^6$ ................................................. A61M 11/00
[52] U.S. Cl. ........................ 128/200.23; 128/203.12
[58] Field of Search ............... 128/200.23, 200.14, 128/203.12, 203.15

[56] References Cited

U.S. PATENT DOCUMENTS

| | | | |
|---|---|---|---|
| 3,187,748 | 6/1965 | Mitchell et al. | 128/200.23 |
| 3,456,644 | 7/1969 | Thiel | 128/200.23 |
| 3,456,645 | 7/1969 | Brock | 128/200.23 |
| 3,456,646 | 7/1969 | Phillips et al. | 128/200.23 |
| 3,565,070 | 2/1971 | Hanson et al. | 128/200.23 |
| 3,598,294 | 8/1971 | Hedrick et al. | 222/402.2 |
| 3,605,738 | 9/1971 | Ciranna | 128/200.23 |
| 3,636,949 | 1/1972 | Kropp | 128/200.23 |
| 3,732,864 | 5/1973 | Thompson et al. | 128/200.23 |
| 3,789,843 | 2/1974 | Armstrong et al. | 128/200.23 |
| 3,814,297 | 6/1974 | Warren | 222/402.13 |
| 5,060,643 | 10/1991 | Rich et al. | 128/200.23 |

FOREIGN PATENT DOCUMENTS

| | | |
|---|---|---|
| 0045419A1 | 8/1982 | European Pat. Off. . |
| 0147028B1 | 5/1988 | European Pat. Off. . |
| 3040641 | 5/1982 | Germany . |
| 155964 | 4/1971 | New Zealand . |
| 1269554 | 4/1972 | United Kingdom . |
| 1335378 | 10/1973 | United Kingdom . |
| 1392192 | 4/1975 | United Kingdom . |
| 2061116 | 5/1981 | United Kingdom . |
| 2240930 | 8/1991 | United Kingdom . |
| 2263873 | 8/1993 | United Kingdom . |
| 2264238 | 8/1993 | United Kingdom . |
| WO92/09323 | 6/1992 | WIPO . |
| WO93/24167 | 12/1993 | WIPO . |

OTHER PUBLICATIONS

U.K. Search Report dated Sep. 16, 1992.
PCT International Search Report dated Dec. 7, 1993.
PCT Written Opinion dated Apr. 12, 1994.
PCT International Preliminary Examination Report dated Aug. 24, 1994.
Troitsky, A. (ed.), "Machine Elements: A Textbook," Foreign Languages Publishing House (Moscow: 1963) pp. 545–553.
Sweet's 1969 Mechanical File, Alco Forge and Spring, Inc. Catalog, pp. 1–7.

Primary Examiner—Edgar S. Burr
Assistant Examiner—Eric P. Raciti
Attorney, Agent, or Firm—Gary L. Griswold; Walter N. Kirn; Dale E. Hulse

[57] ABSTRACT

A breath-actuated aerosol dispenser having a spring to provide the priming force which is held in a partially compressed state within a cage such that the spring applies no force to an aerosol container, valve, or triggering mechanism included in the dispenser while the dispenser is in its rest position.

14 Claims, 7 Drawing Sheets

INHALATION DEVICE

FILED OF THE INVENTION

This invention relates to an inhalation device for administration of medicament in the form of aerosolised solid particles or droplets of liquid or suspension. In particular the invention relates to such devices which are actuated to dispense medicament in response to the patient's inspiration.

BACKGROUND

Asthma and other respiratory diseases have long been treated by the inhalation of appropriate medicament. For many years the two most widely used and convenient choices of treatment have been the inhalation of medicament from a drug solution or suspension in a metered dose pressurised inhaler (MDI), or inhalation of powdered drug generally admixed with an excipient, from a dry powder inhaler (DPI).

Inhalation activatable dispensers for use with aerosol containers which contain medicament and are pressurised with liquid propellants and are equipped with a motoring valve through which a plurality of metered doses may be dispensed are known, their general purpose being to afford proper co-ordination of the dispensing of a dose of medicament with the inhalation of the patient thereby allowing the maximum proportion of the dose of medicament to be drawn into the patient's bronchial passages. Examples of such dispensers are described in British Patent Specification Nos. 269,554, 1,335,378; 1,392,192, 2,061,116 and 2,240, 930 U.S. Pat. Nos. 3,456,644, 3,456,645, 3,456,646, 3,565, 070, 3,598,294, 3,814,297, 3,605,738, 3,732,864, 3,636,949, 3,789,843 and 3,187,748 and German Patent No. 3,040,641.

European Patent No. 147028 discloses an inhalation activatable dispenser for use with an aerosol container in which a latch mechanism releasing vane is pivotally mounted in an air passage between an aerosol outlet valve and a mouthpiece, which latch mechanism cannot be released if force to activate the dispenser is not applied before a patient inhales.

The dispenser generally comprises a housing having a mouthpiece and an air passage therethrough terminating at the mouthpiece, the housing being adapted to receive an aerosol container and having a support block with a socket adapted to receive the stem of the valve of the aerosol container and a through orifice communicating between the socket and the air passage, and latch means having parts movable between an engaged position in which movement of the container and the support block toward each other upon the application of a force to bias the container and the support block toward each other is prevented and a release position in which movement of the container and the support block toward each other in response to said force is permitted causing the stem to move to its inner discharge position, the latch means comprising a vane mounted on the housing in the air passageway between the orifice and the mouthpiece for movement toward the mouthpiece under the influence of inhalation through the mouthpiece to release the latch means in which the vane moves toward the mouthpiece from a blocking to a non-blocking position with respect to the passageway in response to inhaling at the mouthpiece and releases the latch means only during the application of said force to bias the container and support block toward each other.

This inhalation device has been received favourably by patients and doctors since it not only overcomes the hand-lung co-ordination problem but it does so at a very low triggering flow-rate (approximately 30 liters/minute) essentially silently, and with a very compact design barely larger than a standard inhaler.

Many inhalation activatable dispensers utilise a spring to bias the container relative to the valve stem and ultimately move the container relative to the valve stem to fire the device upon inhalation. Generally the spring acts upon the base of the container and is compressed prior to patient inhalation by a priming force generated by operation of a priming lever which may be a separate lever or connected to a pivoting mouthpiece cover. In some arrangements, after activation of the device and removal of the priming force the valve and associated triggering mechanism is reset under the influence of the internal valve spring by movement of the container relative to the valve stem. Thus, in order to ensure efficient operation of the dispenser it is necessary to carefully select the parameters of the biasing spring used to prime the device.

The spring configuration for such a dispenser must exhibit certain specific force characteristics. These characteristics are best described with reference to the three main stages of operation of the device as follows:

The unprimed or at rest stage in which no priming force is applied to the spring and the spring is applying its lowest load to the container. In this position, ideally, the force applied by the spring should be insignificant in the sense that it has no influence on the position of the aerosol container and valve thus allowing the device to reset under the influence of the internal valve spring following the previous actuation. Thus the force applied by the biasing spring must be less than the minimum valve return force.

The priming stage in which the spring is compressed. The force applied by the spring must be greater than that required to fire the aerosol valve but should be kept to a minimum as it governs the magnitude of the inspiratory flow rate required to actuate the dispenser.

The firing stage in which the container is moved relative to the valve sufficiently by the spring to actuate the valve. For correct operation, it is essential that as the spring expands from its primed position it retains sufficient force to overcome the inherent resistance to movement of the valve. Failure at this stage would result in no delivery of medication, The theoretical spring force profile i.e. a plot of force against spring length, is a straight line. In practice, the rate is not linear but tends to increase with compression (the softest parts of the spring compress first). In order to achieve the parameters required for successful dispenser operation, the spring must be selected such that requirements of the unprimed and fired positions are met and in practice this can mean springs generate undesirably high forces in the primed position. Thus, spring selection and manufacturing tolerances are critical.

SUMMARY OF THE INVENTION

The present invention provides an improved spring arrangement for such dispensing devices.

According to the present invention there is provided a breath-actuated aerosol dispenser comprising a housing defining a patient port and containing a pressurised container equipped with a metered dose dispensing valve, primer movable between a rest position and a priming position in which it applies a force sufficient to actuate the dispensing valve and breath-actuated trigger mechanism which prevents actuation of the dispensing valve until a triggering air flow passes through the patient port, in which the primer comprises a spring which is maintained in a partially compressed state when the primer means is in its rest position without applying any substantial force to the aerosol container, valve or breath actuated trigger mechanism.

It has been found that by utilising a spring which is maintained in a partly compressed state, e.g., by restricting the spring within a cage, it is readily possible to achieve the desired spring configuration in all three positions and greatly simplify the manufacture and selection of a suitable spring. By appropriate selection of the cage dimensions it can be guaranteed the spring will not interfere with movement of the aerosol container and valve in the rest position. Furthermore, a spring of free length longer than the available space within the device can be used. This allows the necessary force for the firing stage to be generated at a lower spring rate, which in turn offers the opportunity of either:

a) lowering the force applied in the primed position whilst, maintaining the force generated in the firing stage thus lowering triggering air flow i.e. the inspiratory flow rate required to actuate the dispenser, or b) raising the force generated during the firing stage without adversely affecting the force applied in the priming stage, thus maintaining the triggering inspiratory flow rate at an acceptable level whilst allowing the device to cope with valves requiring more force to actuate.

The cage maintaining the spring in a partially compressed state may be any device having a configuration which allows further compression of the spring when the primer is moved to its priming position. For example, the cage may comprise two interengagable parts having a telescopic action. The parts may be prevented from disengagement by mechanical interlocking between the parts or by separate means e.g. a rivet. Alternatively, the spring may be held in the compressed state by a non-deformable cage provided the priming means has access to the spring. The caged spring constitutes an entirely self-contained system and may be assembled remote from the dispenser in which it is used.

BRIEF DESCRIPTION OF THE DRAWINGS

The invention will now be described with reference to the accompanying drawings in which:

DETAILED DESCRIPTION

Figure 1:
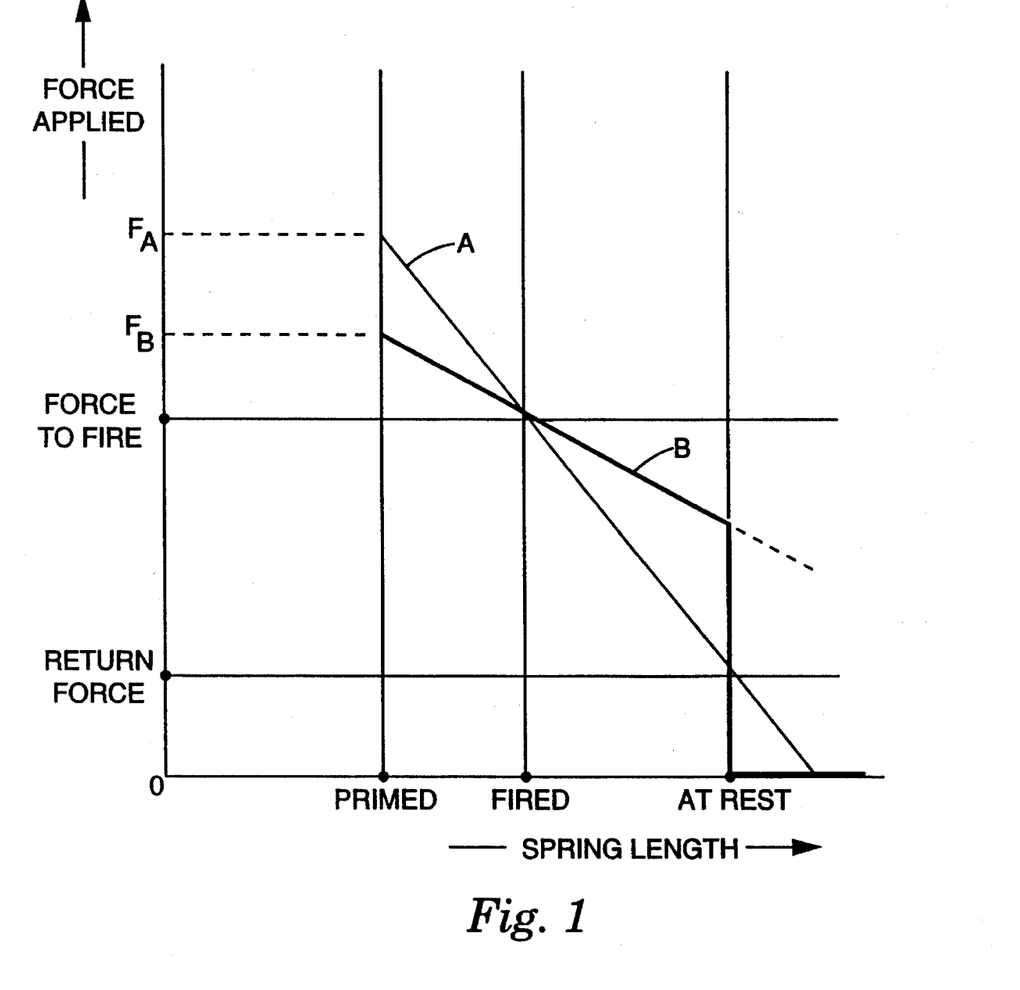
FIG. 1 represents a plot of force applied against spring length for unrestricted and caged springs.

FIG. 1 is a plot of force applied by a spring against spring length. The plot indicates the force to fire which is that force required to move the aerosol container relative to the valve for actuation of the valve, and the return force which is the force generated by the internal spring of the valve.

Plot A is the force profile of an unrestricted spring. In its at rest position the force applied by the spring must not exceed the return force generated by the internal spring of the valve or the device will not reset. In the firing stage the force applied by the spring must be sufficient to move the container relative to the valve. In a theoretically perfect spring the force profile will be a straight line and accordingly, if the criteria in the at rest and fired positions are met the force applied by the spring in the primed condition will be $F_A$. This force should be ideally kept as low as possible in order to allow the device to be activated by low inspiratory flow rates. In practice, the profile of a spring is not often a straight line and there is a tendency for $F_A$ to be considerably higher.

Plot B illustrates the force profile of a caged spring. The spring is maintained in a partially compressed state by a cage and accordingly in its at rest position will apply no force against the aerosol container. At its restrained length, in absence of the cage, the spring would apply a force higher than the return force and this is represented in the plot by a step at the at rest position. The use of the caged spring allows a lower rated, longer spring to be used and thus the straight line portion of the profile may have a shallower slope than that of Plot A, retaining the necessary force to fire in the firing stage, but applying a force $F_S$ which is considerably lower than $F_A$ in the primed position. Thus, it is possible to maintain triggering inspiratory flow rates at lower levels using a caged spring than could be achieved using an unrestricted spring.

Figure 2A:
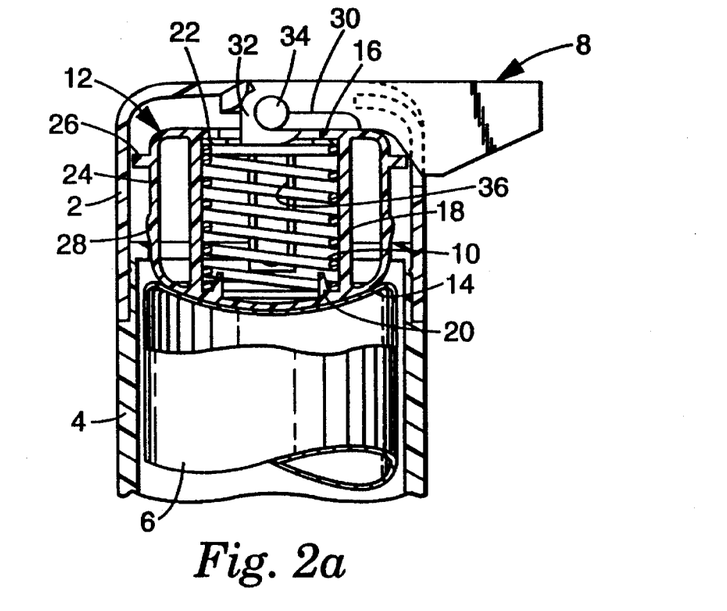
FIGS. 2a to 2c represent a section through the primer means of an aerosol dispenser in the at rest, priming and firing stages respectively.
Figure 2B:
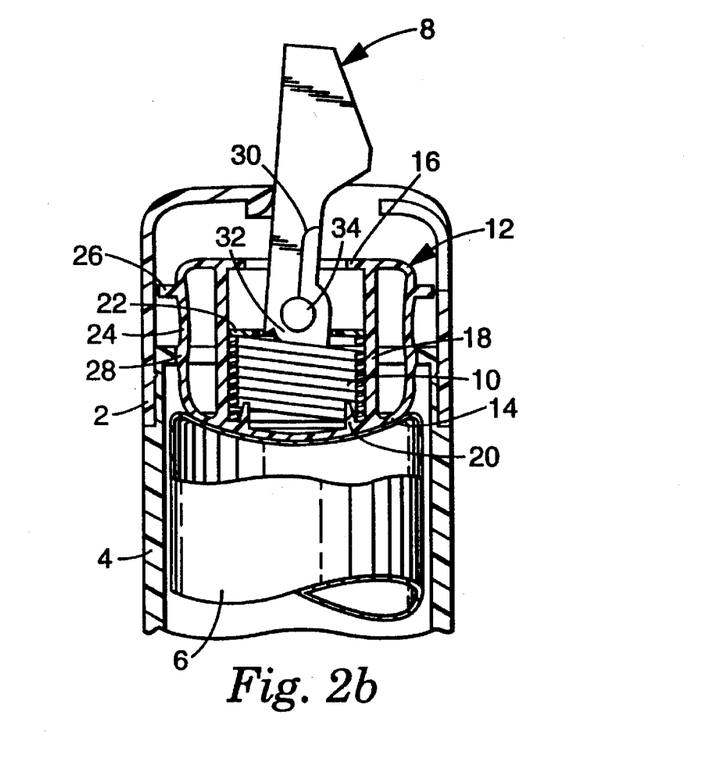
Figure 2C:
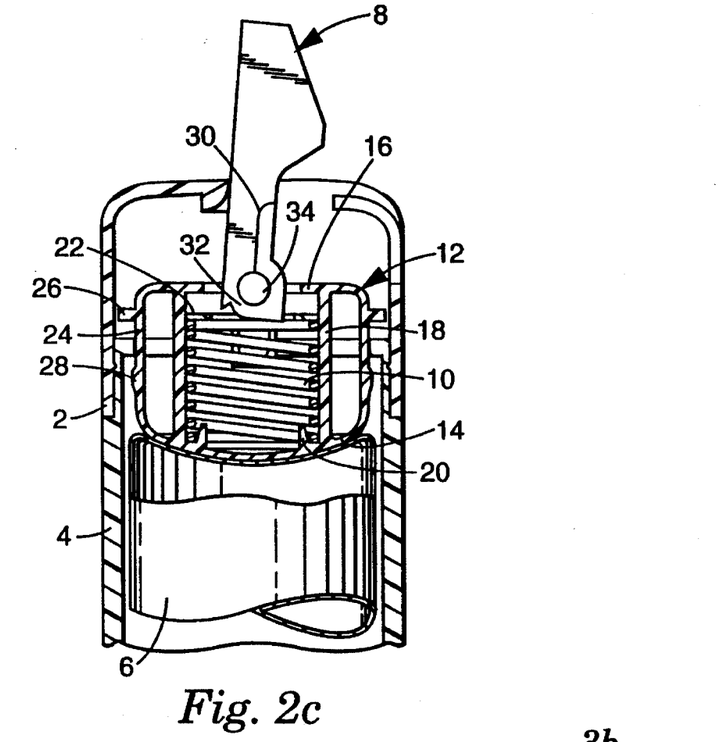

FIGS. 2a to 2c represent cross-sections through the upper part of a breath-actuated aerosol dispenser illustrating the priming means of the device. The device comprises a housing formed of parts (2 and 4) within which an aerosol container partly shown at (6) is positioned. The device additionally comprises breath-actuated trigger (not shown), e.g., of the type disclosed in European Patent No. 147028, the full disclosure of which is incorporated herein by reference.

The primer of the device comprises a priming lever (8) which acts on spring (10) held within a cage (12). The cage (12) comprises a base (14) and shoulder portions (16) joined by side portions (18). The side portion (18) may be in the form of a substantially cylindrical wall or may comprise a plurality of upright portions. The distance between the base (14) and shoulder (16) is less than the unrestrained length of the spring (10) and accordingly, the spring (10) will always be in the partially compressed state when it is confined in the cage. The base portion (14) is shaped to configure to the base of the aerosol container (6) and may comprise internal lugs (20) to facilitate correct positioning of the spring within the cage. The cage may additionally comprise a circular plate or washer (22) positioned beneath the shoulder portions (16) and movable within the cage to apply pressure to the spring (10).

FIG. 2a shows the device in the at rest or unprimed position. The cage is dimensioned such that it fits in the space between the base of the aerosol container (6) and the priming lever (8) without applying pressure to the base of the aerosol container. The cage (10) may possess resilient guide portions (24) having projections (26, 28) to ensure the cage and spring are correctly aligned in the device and to prevent unwanted movement of the cage during transportation and handling of the device.

FIG. 2b shows the device in the primed position. Priming is effected by upward movement of the priming lever (8). The lever (8) comprises a cam surface (30) which engages the undersurface of the housing (2) causing the end (32) of the priming lever to move downwardly. The priming lever (8) comprises lugs (34) which engage within channels (36) within the housing (2) to control the movement of the priming lever. As the end (32) of the priming lever moves it causes movement of the washer (22) within the cage (12) which in turn causes compression of the spring (10). In the primed position the spring will be under its maximum compression and the force applied to the aerosol container (6) will be in excess of the force required to actuate the aerosol valve. Movement of the container (6) is prevented by the breath-actuated trigger (not shown) which blocks movement of the container until patient inspiration, when a triggering air flow passes through the patient port. Those skilled in the art will recognise that the air flow that constitutes a triggering air flow will depend on the particular breath-actuated dispenser and the particular trigger. Generally, however, flow rates of 15 to about 60 L/min are sufficient to actuate a device and ensure delivery of the drug to the lung of the patient.

FIG. 2c shows the device in its fired position. Upon inspiration the trigger moves to an unblocking position allowing movement of the aerosol container (6). The aerosol container (6) is moved downwardly under the influence of the spring (10) which acts on the cage (12) thereby actuating the valve and firing a dose of medicament. When the priming lever (8) is moved to the unprimed or rest position (FIG. 2a) the force developed by the internal spring of the aerosol valve is sufficient to move the aerosol container (6), cage (12) and spring (10) upwardly to the at rest position shown in FIG. 2a.

As seen in FIGS. 2a–2c, the shoulder portions (16) of cage (12) are provided as a top element of the cage and are integrally connected to base (14) which is provided as a bottom element of cage (12), such that such top and bottom portions of the cage form an integral structure. As disclosed herein and as shown in FIG. 2a, the top element of cage (12) represented by shoulder portions (16) engages the top end of spring (10), and the bottom element of cage (12) represented by base (14) with its internal lugs (20) engages a bottom end of spring (10) so as to hold spring (10) in a partially compressed state when the primer is in its rest position. In addition, as is apparent from the disclosure herein as well as from FIGS. 2a–2c, both the top element and bottom element of cage (12), as well as the entire structure making up cage (12), are movable within the housing defined by parts (2) and (4).

Figure 3A:
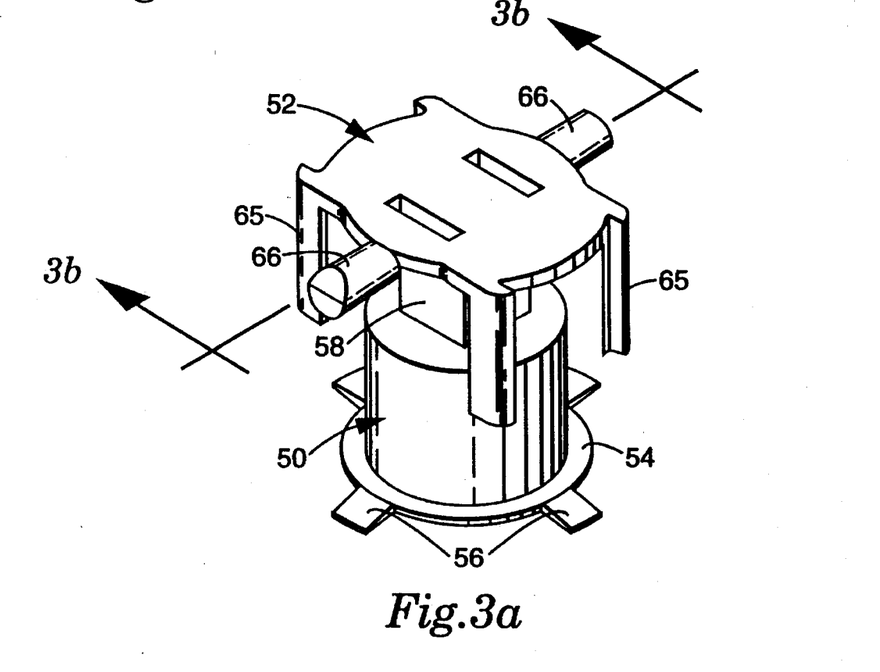
FIGS. 3a and 3b represent a perspective and sectional view through a caged spring arrangement suitable for use in the invention.
Figure 3B:
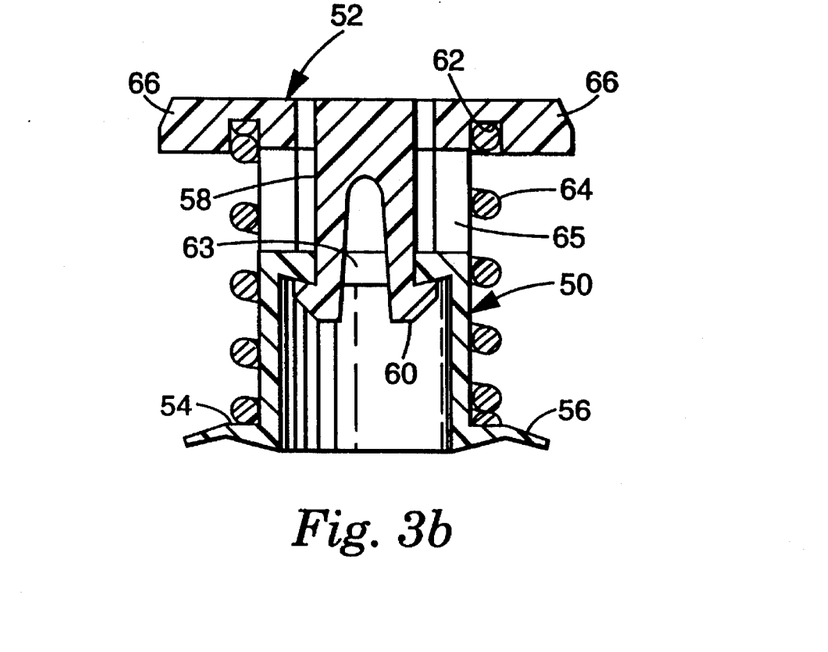

It will be readily appreciated the cage for the spring may have numerous configurations and may be used with different types of compression spring, e.g., cylindrical, conical etc. FIGS. 3a and 3b illustrate an alternative embodiment of a cage and spring arrangement. The cage comprises interengaged lower (50) and upper (52) components. The lower component (50) is substantially cylindrical in shape having a base flange (54) and a plurality of feet (56). The upper portion (52) has a stem (58) terminating in compressible lugs (60) which are accommodated within an aperture (63) in the lower component to allow telescopic movement of the upper and lower components without separation. The upper component (52) has a shoulder region (62) and the spring (64) is held in a partially compressed state between the base flange (54) and shoulder (62) (FIG. 3a). The upper portion (52) has a plurality of guide legs (65) and projections (66) which engage in corresponding slots in the interior of the housing of the device to facilitate correct alignment caged spring arrangement. The priming lever of the aerosol device acts on the upper component (52) pushing this component downwardly to compress the spring.

Figure 4:
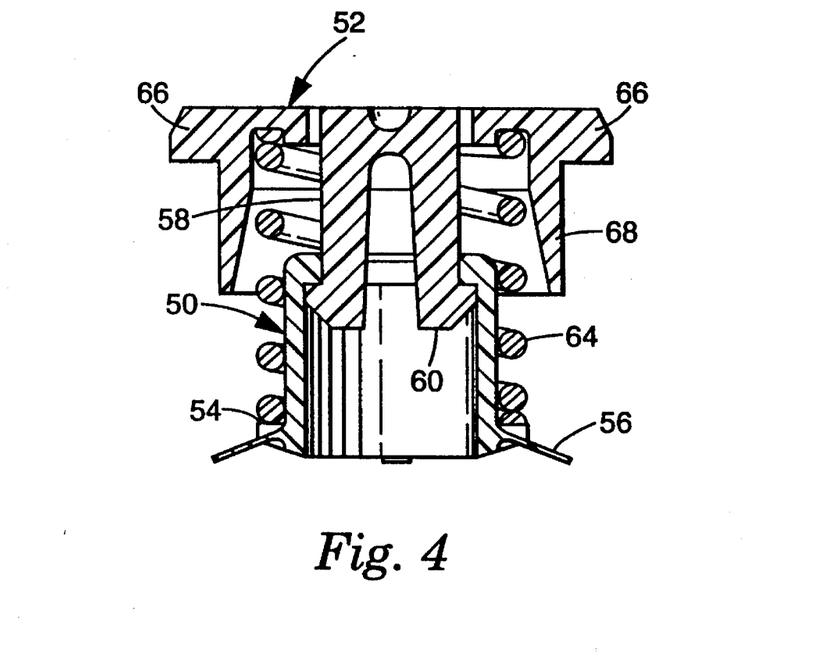
FIG. 4 represents a sectional view through a further caged sprang arrangement in accordance with the invention.

The caged spring arrangement of FIG. 4 is similar to that disclosed in FIGS. 3a, 3b, like numerals represent like parts. The feet (56) are flexible and project downwardly in order to ensure the cage fully occupies the space between the aerosol container and priming lever so that the cage will not rattle when the priming lever is in the unprimed position and the device is carried by a patient, e.g., in a pocket, handbag etc. A further difference is the provision of an annular wall (68) in place of the guide legs (65).

Figure 5:
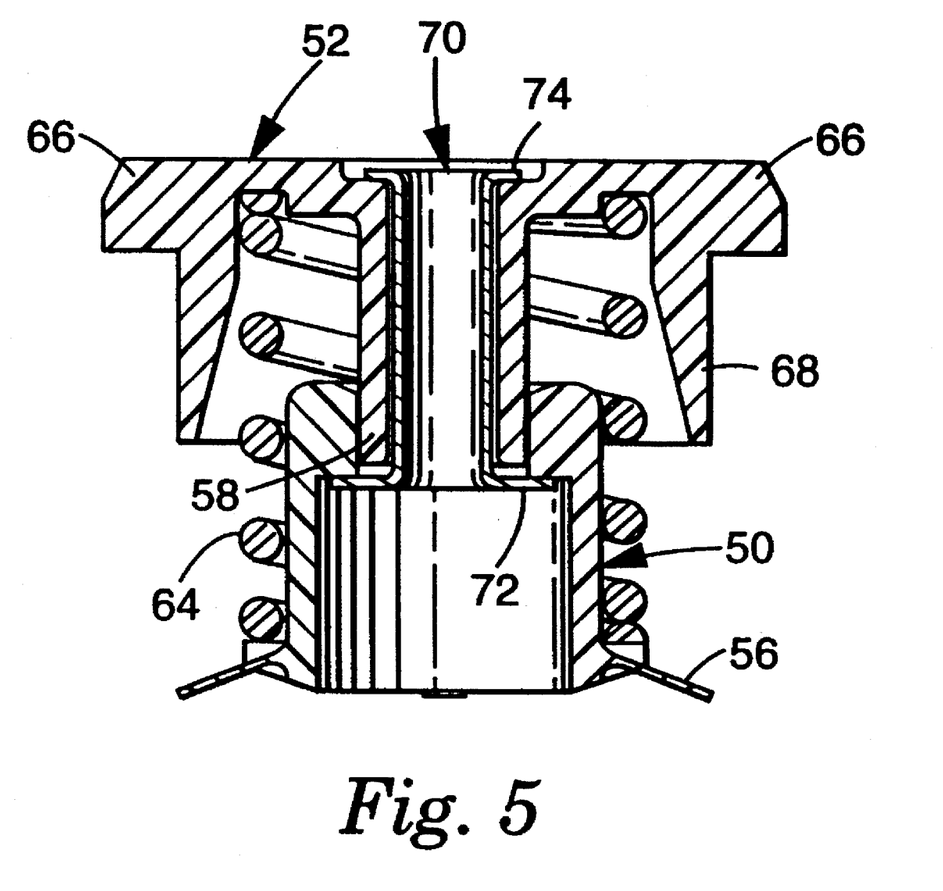
FIG. 5 represents a sectional view through a further caged spring arrangement in accordance with the invention.

The caged spring arrangement of FIG. 5 is similar to that disclosed in FIGS. 3a, 3b and 4. The fundamental difference is that the upper portion (52) and the lower portion (50) are held together by a rivet (70) having upper and lower flanges (74,72) engaging the upper and lower portions (52,50) preventing, disengagement. The upper and lower portions are free to telescope along the length of the rivet (70) for further compression of spring (64) when the dispenser is primed.

Figure 6:
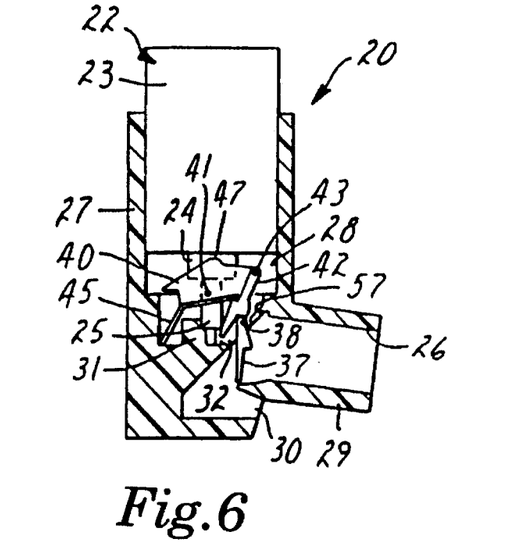
Figure 7:
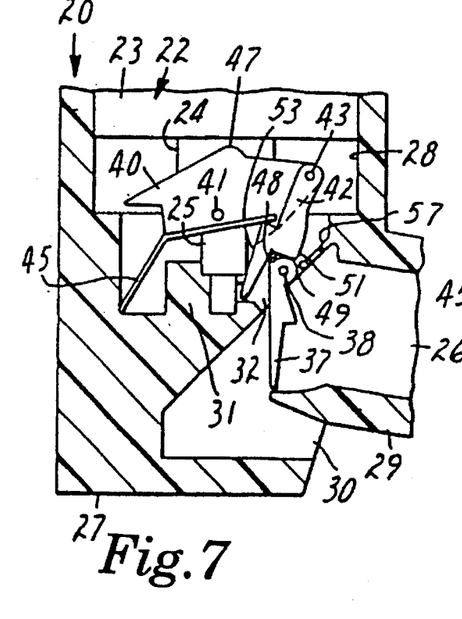

As mentioned previously, a typical breath-actuated trigger mechanism and metered dose dispensing valve which may be used in connection with the present invention are illustrated in European Patent No. 147,028 which was granted on May 4, 1988, the disclosure of which has been incorporated by reference herein. A portion of that disclosure is repeated hereinafter in connection with FIGS. 6–12 to describe such breath-actuated trigger mechanism and metered dose dispensing valve (note that the reference numerals referenced hereinafter refer only to the drawings set forth in FIGS. 6–12, and such reference numerals do not relate to FIGS. 1–5):

As is best seen in FIG. 6, the dispenser 20 is adapted for use with an aerosol container assembly 22 of the known kind including a container 23 containing a medicament and liquid propellant, and a metering valve 24 (such as described in U.S. Pat. No. 3,598,294) fixed in one end of the container 23 for dispensing a metered dose of the medicament from the container 23 through a hollow stem 25 included in the valve 24. The stem 25 is movable relative to the container 23 between an outer charging position (to which the stem 25 is biased by a spring in the valve 24) and an inner discharging position at which a metered dose is discharged through the stem 25.

The dispenser 20 comprises a housing 27 defining an open ended chamber 28 into which the container assembly 22 may be inserted stem 25 down, a mouthpiece 29, and a through air passage 26 extending from an inlet opening 30 adjacent the mouthpiece 29 to an outlet through the mouthpiece 29. The housing includes a nozzle block 31 having a socket adapted to receive the stem 25, and a through orifice 32 adapted to direct medicament and liquid propellant from the stem 25 into the air passageway 26. Thus upon manual movement of the container 23 toward the block 31 the stem 25 will be moved to its discharging position relative to the container 23 so that medicament is discharged through the orifice 32 into the air passageway 26 toward the mouthpiece for inhalation by the patient. To prevent any escape of the medicament and propellant upwardly out of the nozzle block 31, and to accommodate a certain variation in sizes of stems 25, the dispenser 20 may include a soft seal gasket (not shown) located in the nozzle block 31.

In order to coordinate the dispensing of the medicament with the inhalation of a patient, the dispenser is provided with a latch mechanism including a vane 37 mounted on the housing 27 for a pivotable movement about an axis 38 between a blocking position blocking a portion of the air passageway 26 between the orifice 32 in the nozzle block 31 and the mouthpiece 29 (FIGS. 6, 7 and 8) and a non-blocking position (FIGS. 10, 11, and 12) at one side of and not blocking the air passageway 26.

The latch mechanism also comprises a rocker 40 mounted on the housing 27 for pivotal movement about a fulcrum 41, and a catch 42 mounted on the rocker 40 for pivotal movement about an axis 43 spaced from the rocker fulcrum 41. When the dispenser 20 is not in use or in a normal condition (FIGS. 6 and 7) the container assembly 23 is spaced from the rocker 40 by the internal valve spring in the metering valve 24. The rocker 40 has an integrally formed spring 45 which normally positions the rocker 40 in an initial position at which the catch 42 is held over, but spaced from the vane 37.

Figure 8:
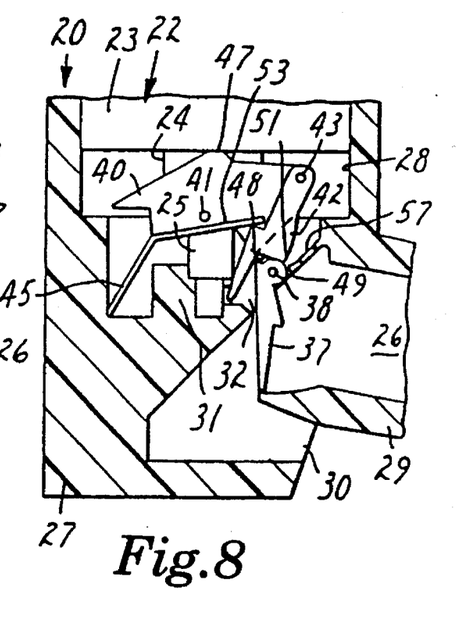
Figure 9:
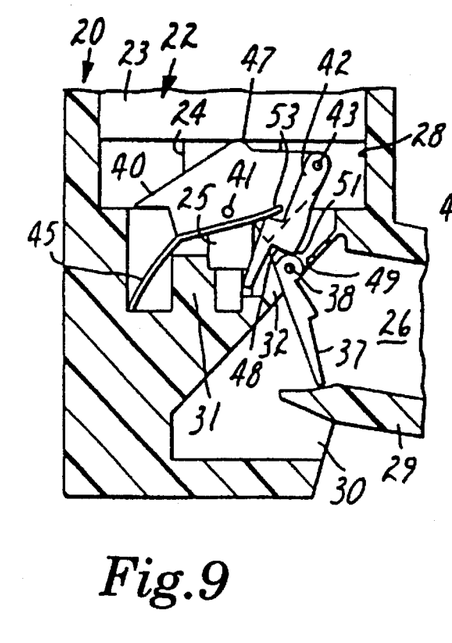
Figure 10:
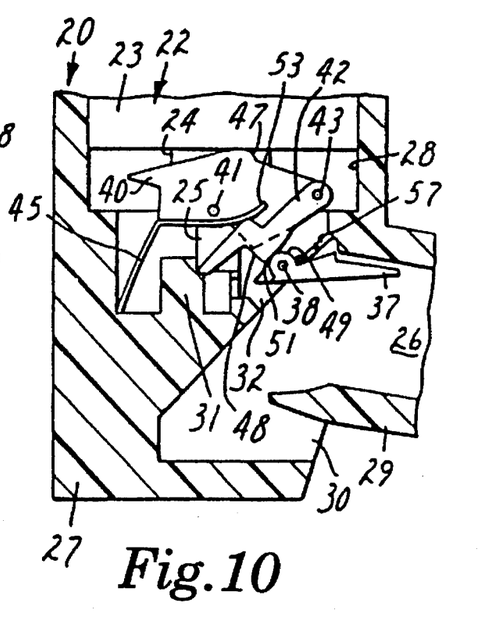
Figure 11:
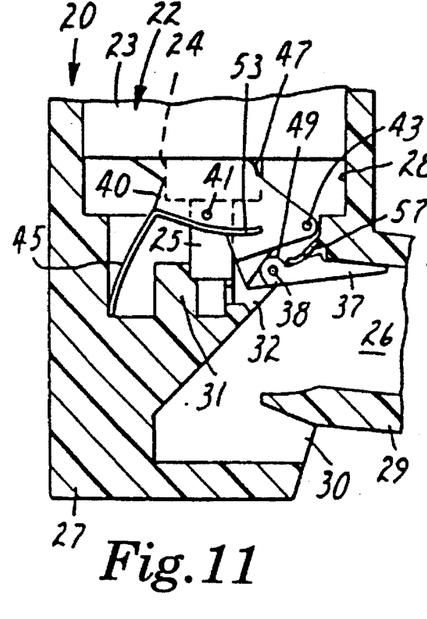
Figure 12:
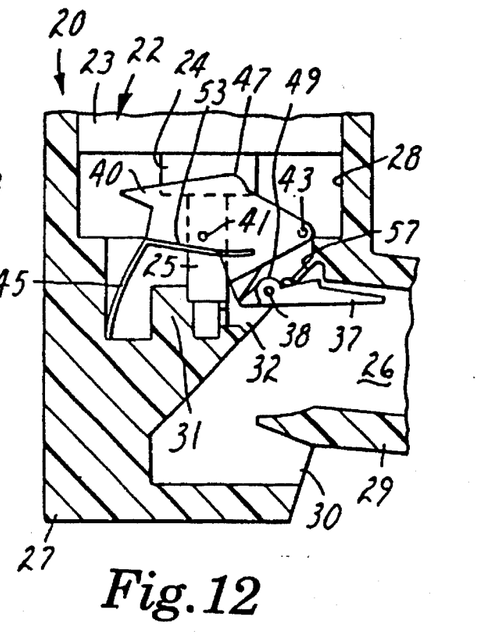

To operate the dispenser 20, a user first presses the container 23 into the chamber 28 in the housing 27 until the container 23 contacts the rocker 40 at a point 47 close to the fulcrum 41 and rotates the rocker 40 through a small angle about the fulcrum 41 to a retaining position at which further rotation of the rocker 40 or movement of the container 23 is prevented by the engagement between a shoulder 48 of the catch 42 and an edge surface 49 of the vane 37 to produce a cocked condition for the dispenser 20 (FIG. 8). The latch mechanism is then engaged to prevent further movement of the container 23 toward the nozzle block 31 by the applied force until inhalation by the user through the mouthpiece 29 moves the vane 37 from its blocking to its nonblocking position to release the latch mechanism and allow the container 23 to be further depressed relative to the stem 25 held in the block 31 to dispense a dose of medicament.

We claim:

1. A breath-actuated aerosol dispenser comprising a housing defining a patient port and containing an aerosol container equipped with a metered dose dispensing valve, a primer movable between a rest position and a priming position in which it applies a force sufficient to actuate the dispensing valve, and a breath-actuated trigger mechanism which prevents actuation of the dispensing valve until a triggering air flow passes through the patient port, wherein the primer comprises a spring and a cage, the spring being positioned within the cage such that the spring is maintained in a partially compressed state when the primer is in its rest position and such that no substantial force is applied by the spring to the aerosol container, dispensing valve, or breath-actuated trigger mechanism in the rest position, the cage comprising a top element which engages a top end of the spring and a bottom element which engages a bottom end of the spring so as to hold the spring in said partially compressed state when the primer is in its rest position, said top element and said bottom element of the cage being movable within the housing.

2. A dispenser as claimed in claim 1 wherein the cage and spring are configured and positioned such that the spring applies no force to the aerosol container, dispensing valve, or breath-actuated trigger mechanism when the primer is in its rest position.

3. A dispenser as claimed in claim 1 wherein the primer additionally comprises a lever having a cam surface, said lever being pivotally mounted in the housing such that pivotal movement of the lever from a rest to a priming position causes additional compression of the spring which applies a priming force to the aerosol container or dispensing valve.

4. A dispenser as claimed in claim 1 wherein the top element of the cage is integrally connected to the bottom element of the cage to form an integral structure.

5. A dispenser as claimed in claim 4 wherein the primer additionally comprises a lever having a cam surface, said lever being pivotally mounted in the housing such that pivotal movement of the lever from a rest to a priming position causes additional compression of the spring which applies a priming force to the aerosol container or dispensing valve.

6. A dispenser as claimed in claim 5 wherein the cage and spring are configured and positioned such that the spring applies no force to the aerosol container, dispensing valve, or breath-actuated trigger mechanism when the primer is in its rest position.

7. A dispenser as claimed in claim 1 wherein the cage comprises two interengaged parts capable of relative movement to allow further compression of the spring when the primer is moved to its priming position.

8. A dispenser as claimed in claim 7 wherein the two parts of the cage are configured so as to have a telescopic action with respect to each other.

9. A dispenser as claimed in claim 8 wherein the primer additionally comprises a lever having a cam surface, said lever being pivotally mounted in the housing such that pivotal movement of the lever from a rest to a priming position causes additional compression of the spring which applies a priming force to the aerosol container or dispensing valve.

10. A dispenser as claimed in claim 5 wherein the cage and spring are configured and positioned such that the spring applies no force to the aerosol container, dispensing valve, or breath-actuated trigger mechanism when the primer is in its rest position.

11. A dispenser as claimed in claim 7 wherein the cage further comprises a rivet and wherein the two interengaged parts are prevented from disengaging by means of the rivet.

12. A dispenser as claimed in claim 11 wherein the primer additionally comprises a lever having a cam surface, said lever being pivotally mounted in the housing such that pivotal movement of the lever from a rest to a priming position causes additional compression of the spring which applies a priming force to the aerosol container or dispensing valve.

13. A dispenser as claimed in claim 12 wherein the cage and spring are configured and positioned such that the spring applies no force to the aerosol container, dispensing valve, or breath-actuated trigger mechanism when the primer is in its rest position.

14. A dispenser as claimed in claim 1 wherein the spring is a cylindrical coil spring.

* * * * *

UNITED STATES PATENT AND TRADEMARK OFFICE
CERTIFICATE OF CORRECTION

PATENT NO.: 5,511,540
DATED: April 30, 1996
INVENTOR(S): Andrew M. Bryant et al.

It is certified that error appears in the above-identified patent and that said Letters Patent is hereby corrected as shown below:

Col. 1, line 2, "FILED" should be --FIELD--.

Col. 1, line 22, "motoring" should be --metering--.

Col. 1, line 30, "269,554" should be --1,269,554--.

Col. 3, line 59, move the heading "DETAILED DESCRIPTION" from col. 3, line 59 to be inserted after line 62 in col. 3.

Col. 6, line 15, after "preventing" delete the comma.

Col. 8, line 39, in claim 10, line 1, "5" should be --9--.

Signed and Sealed this

Fifteenth Day of October, 1996

Attest:

BRUCE LEHMAN

Attesting Officer

Commissioner of Patents and Trademarks